(12) United States Patent
Taveira et al.

(10) Patent No.: US 7,442,236 B2
(45) Date of Patent: Oct. 28, 2008

(54) XENON EXTERNAL RECYCLING UNIT FOR RECOVERY, PURIFICATION AND REUSE OF XENON IN ANAESTHESIA CIRCUITS

(75) Inventors: Antonio Pedro Grilo Taveira, Oporto (PT); Adélio Miguel Magalhães Mendes, Oporto (PT)

(73) Assignee: Sysadvance-Sistemas de Engenharia, S.A., Moreira da Maia (PT)

( * ) Notice: Subject to any disclaimer, the term of this patent is extended or adjusted under 35 U.S.C. 154(b) by 235 days.

(21) Appl. No.: 10/513,047

(22) PCT Filed: Apr. 30, 2003

(86) PCT No.: PCT/EP03/04568

§ 371 (c)(1),
(2), (4) Date: Jun. 29, 2005

(87) PCT Pub. No.: WO03/092778

PCT Pub. Date: Nov. 13, 2003

(65) Prior Publication Data

US 2005/0235831 A1    Oct. 27, 2005

(30) Foreign Application Priority Data

May 2, 2002    (PT) .................................... 102772

(51) Int. Cl.
*A61M 16/01* (2006.01)
*B01D 53/02* (2006.01)

(52) U.S. Cl. ............... 96/111; 96/134; 128/205.12; 128/205.28

(58) Field of Classification Search ............... 96/109, 96/111, 121, 134; 95/116, 130, 139, 903; 128/202.22, 203.12, 205.12, 205.27, 205.28
See application file for complete search history.

(56) References Cited

U.S. PATENT DOCUMENTS

| 4,989,597 | A | | 2/1991 | Werner |
| 5,039,500 | A | * | 8/1991 | Shino et al. ................. 423/262 |
| 5,186,007 | A | * | 2/1993 | Takano et al. ................. 62/656 |
| 5,520,169 | A | | 5/1996 | Georgieff et al. |
| 6,095,137 | A | * | 8/2000 | Wallroth et al. ........ 128/203.26 |
| 6,236,041 | B1 | | 5/2001 | Donnerhack et al. |
| 6,471,747 | B1 | * | 10/2002 | Venkatesh et al. .............. 95/90 |
| 2003/0000385 | A1 | | 1/2003 | Kawai et al. |
| 2003/0106335 | A1 | * | 6/2003 | Golden et al. ................. 62/648 |

FOREIGN PATENT DOCUMENTS

| WO | WO 97/20591 | * | 6/1997 |
| WO | WO 01/07108 A1 | | 2/2001 |
| WO | WO 02/32550 A1 | | 4/2002 |

* cited by examiner

*Primary Examiner*—Frank M Lawrence
(74) *Attorney, Agent, or Firm*—Saliwanchik, Lloyd & Saliwanchik

(57) ABSTRACT

The present invention concerns the application of adsorption gas separation technologies to anaesthesia equipment and falls within the technical domains of adsorption separation units and medical devices. The invention concerns a device and processes for recovering xenon from gas mixtures released from anaesthesia gas machines (1) using xenon as anaesthetic. The purged xenon is collected using a system which includes a shift valve (6), and then separated and purified (38-40). The recycled xenon is then pressurised (31) and reintroduced in the anaesthesia circuit (48) using a shift valve (12). The separation and purification process combines different adsorption separation/purification technologies. The device is external to the anaesthesia gas machine and is compatible with any standard anaesthesia circuit able of perform xenon anaesthesia.

15 Claims, 4 Drawing Sheets

XENON EXTERNAL RECYCLING UNIT FOR RECOVERY, PURIFICATION AND REUSE OF XENON IN ANAESTHESIA CIRCUITS

This application is a National Stage Application of International Application Number PCT/EP03/04568, filed Apr. 30, 2003; which claims priority to Portugal Application No. PT 102772, filed May 2, 2002.

FIELD OF THE INVENTION

The present invention concerns the application of adsorption gas separation technologies to anaesthesia equipment and falls within the technical domains of adsorption separation units and medical devices. The invention concerns a device and processes for selectively recovering xenon from gas mixtures released from anaesthesia gas machines (1) using xenon as anaesthetic. The purged xenon is collected, purified and then conditioned for reuse. The device is external to the anaesthesia gas machine and is compatible with any standard anaesthesia circuit able of perform xenon anaesthesia.

BACKGROUND OF THE INVENTION

Xenon is a very efficient anaesthetic gas, however it is an expensive and a rare resource. Recycling can significantly reduce the high costs associated with its use as anaesthetic. Two different xenon-recycling approaches can be taken: internal recycling (performed inside the Anaesthesia Gas Machine—AGM) and external recycling (performed outside the Anaesthesia Gas Machine—AGM). Two solutions have been proposed for internal recycling (bibliography [1] and [2]): the first proposed by University of Porto (Faculty of Engineering—FEUP), considers the constant removal of carbon dioxide and nitrogen from a closed circuit AGM, using adsorption and/or membrane technology; the second, proposed by Nippon Oxygen Corporation, considers only the removal of nitrogen, consequently reducing the AGM purge waste.

Two different kind of technological solutions have been proposed for xenon external recycling:

High-pressures and/or cryogenic technologies—bibliography [3] to [7].

Adsorption based technologies—bibliography [8] and [9].

The first kind requires the manipulation of pressure and/or temperature in order to condensate xenon from the anaesthetic gas mixture. This process is used thoroughly in xenon industrial separation from air, however, the high volume, noise and power consumption of the required equipment make this process less attractive for smaller scales.

The second kind requires the use of specific adsorbents in order to selectively adsorb some of the components of the anaesthetic gas mixture. After treatment, the recycled xenon is usually pressurized in a gas cylinder.

SUMMARY OF THE INVENTION

Anaesthesia Gas Machines (AGMs) are used whenever it is necessary to perform gaseous anaesthesia. These devices deliver a precisely-known but variable-gas mixture, including anaesthetizing and life-sustaining gases.

Usually two types of AGMs are used for xenon anaesthesia: closed-loop AGMs and low-flow AGMs.

In closed-loop AGMs, the anaesthetic gas mixture circles in a closed-loop circuit being the gas mixture continuously fed to the patient. During the breathing process the patient inhales oxygen exhaling carbon dioxide and nitrogen. Carbon dioxide is continuously removed from the anaesthetic circuit by absorption containers (usually containing soda lime). The required oxygen concentration is continuously restored by the control system of the anaesthetic circuit. The nitrogen continuously exhaled by the patient builds-up in the closed loop. When its concentration reaches approximately 5% it becomes a problem and the whole anaesthetic gas mixture is purged and a new mixture is supplied. Usually the purged anaesthesia gas mixture is disposed of outside the Operation Room (OR) through an external ventilation system (European standards DIN13260 or EN740). Frequently, pure oxygen is previously given to the patient in order to remove the nitrogen in his body, this removal is not complete and therefore the referred purges are necessary.

In, low flow AGMs the flow of anaesthetic gas mixture supplied to the patient is slightly above his breathing needs. Exhaled and excess flows are purged from the anaesthetic circuit. Carbon dioxide can be totally removed using an absorption system. The purged gas mixture is usually disposed of through an exterior ventilation system.

In an average surgery approximately 13.5 litres of xenon are spent. The purpose of the present invention is the recovering and recycling the xenon released from the anaesthetic circuits for being reused in the circuit. The proposed Xenon External Recycling Unit (XERU) is completely external and independent from the AGM, i.e. it does not interfere with the anaesthetic gas mixture circulation during anaesthesia, nor with any of the AGM functionality, either if the Xenon External Recycling Unit (XERU) is activated or not.

The sketch in FIG. 1, illustrates the proposed device and process, which are based in the following stages:

The Selective Recovery System (SRS) of the anaesthetic gas mixture released by the AGM;

a condensation removal system;

a gas sterilisation system;

a System of Purification (SP) of the xenon present in the stored anaesthetic gas mixture;

a composition detector;

a Recycled Xenon Introduction System (RXIS).

The anaesthetic gas mixture is recovered through a gas line connecting the Anaesthesia Gas Machine (AGM) vent relief valve to the Xenon External Recycling Unit (XERU) (1). The purged anaesthetic gas mixture, containing xenon, is recovered instead of being disposed of through the external ventilation system (49). The recovery is performed by a Selective Recovery System (SRS).

The Selective Recovery System (SRS) comprises a flowmeter (either a mass or a volumetric flowmeter), a composition detector and a 3-way valve. The 3-way valve (6) can be either activated or not; if activated the valve connects the Anaesthesia Gas Machine (AGM) to the Xenon External Recycling Unit (XERU), if not it connects the Anaesthesia Gas Machine (AGM) to the external ventilation system. By default, the valve is not activated, when so, the Xenon External Recycling Unit (XERU) does not interfere with the Anaesthesia Gas Machine (AGM) purge, this corresponds to the safer position.

If the Xenon External Recycling Unit (XERU) power supply is cut, if the Xenon External Recycling Unit (XERU) maximum capacity of treatment/storage of anaesthetic gas mixture is reached, if any abnormal situation occurs or if the anaesthetist decides to, the 3-way valve is deactivated and the anaesthetic gas mixture is directed to the external ventilation system. Under standard operation conditions, the valve is activated if the gas stream released by the Anaesthesia Gas Machine (AGM) has a minimum flow and a minimum xenon composition.

During the surgery the xenon composition in the purged anaesthetic gas mixture fluctuates. The Selective Recovery System (SRS) allows narrowing the xenon composition range of the anaesthetic gas mixture treated by the System of Purification (SP).

The anaesthetic gas mixture collected by the Selective Recovery System (SRS) is directed through a filter system (13-14) which full removes bacteria and reduces all the condensable present in the anaesthetic gas mixture up to a molar concentration below 0.5%. The main condensable are usually water vapour, volatile organic compounds and high-powerful anaesthetics (fluoranes). There are several commercially available options for condensable removal: membrane filters, adsorption filters, driers, etc.

The filtered anaesthetic gas mixture, mainly composed of xenon, oxygen and nitrogen, is directed to a packed column (38), which is filled with a selective adsorbent, e.g. zeolite 5A, and has a hole in each end. The first hole is for feeding the filtered anaesthetic gas mixture and the second is the exit. The adsorbent filled packed column can selectively retain high-quantities of xenon in a small volume at low pressures.

The adsorbent in packed column selectively absorbs more xenon than oxygen and nitrogen. It was experimentally verified (FIG. 2) that zeolite 5A adsorbs 5 times more xenon than nitrogen and 14 times more xenon than oxygen (at 1 atm).

The packed column must be previously evacuated before the anaesthetic gas mixture is fed. The xenon contained in the fed anaesthetic gas mixture is selectively adsorbed in the packed column; the remaining gases leave column and are disposed of. When the capacity of the adsorbent is reached, the packed column stops retaining xenon which leaves the column (FIG. 3). Before this happens, the column should be isolated to prevent xenon losses.

A 3-way valve (7) allows directing the gas leaving the packed column either to be disposed of through an external ventilation system (49), if the xenon concentration is below a certain threshold or to a purification unit, otherwise. The xenon concentration in the gas stream leaving the column is analysed using a concentration detection system (4).

When the packed column was filled with 2 kg of zeolite 5A, it was possible to treat 112 litres (STP) of anaesthetic gas mixture (equivalent to the amount of gas purged in 5 to 6 average surgeries) containing 70%-24%-6% of xenon-oxygen-nitrogen at a pressure of 1.4 bara. It was possible to remove more than half of the oxygen-nitrogen present in the gas mixture with xenon losses below 5%.

Since the composition of the purged anaesthetic gas mixture is not constant, a detection system at the exit of the packed column is used to prevent xenon losses. This detection system can either be a composition sensor or a temperature sensor, placed near the column end, that detects the heat released during xenon adsorption.

When the packed column is filled to capacity, the comprised gas mixture is removed and the xenon is purified. This is performed using a vacuum pump or/and a heating system.

Xenon is purified in an adsorption system using Vacuum Swing Adsorption (VSA), in which the adsorbent selectively retains all components but xenon, and the adsorbent is regenerated by total pressure decrease. Separation is achieved using a carbon molecular sieve (e.g. Takeda CMS, Japan), a kinetic adsorbent (i.e. based on the different diffusion times of the gases in the adsorbent).

The gas stream to be treated has an average xenon composition of 70%, being the remaining components oxygen, nitrogen and residual amounts (below 0.5%) of fluoranes, water vapour and volatile organic compounds. Breakthrough experiments with Takeda's CMS using a gas mixture containing 70%-24%-6% of xenon-oxygen-nitrogen, showed a low retention time for xenon, indicating that this gas is not significantly adsorbed (FIG. 4); on the other hand, oxygen, nitrogen and carbon dioxide are strongly adsorbed.

For the mentioned fed composition, the VSA unit can achieve a xenon purity of 97% or above with a xenon recuperation above 70%. This is performed using the following procedure.

The unit consists in a pair of packed columns filled with a selective adsorbent (e.g. Takeda's CMS) operating in a 180° out of phase cycle, comprising the following sequential steps:

a) a pressurisation step, lasting for 1 to 20 seconds, in which the pressure inside the packed column is increased from a sub-atmospheric pressure to a given pressure, first by using a gas stream from the other column and then using the gas stream to be recycled; the column end opposite to the feed end is kept closed;

b) a production step, lasting less than 10 minutes, in which the gas stream is fed to one end of the packed column, and a rich xenon concentration stream is produced on the other end of the column by retaining the non-xenon components in the adsorbent; this step is finished when the adsorbent has no longer capacity to retain the non-xenon fed components;

c) an equalisation step, in which the gas mixture, containing xenon, present in the packed column inter-particular phase is recovered in the second column, by connecting the two columns and allowing the pressurised gas mixture to flow to the evacuated second column until pressure in both columns is partially or totally equalised;

d) an evacuation step, succeeding the equalisation step, in which the packed column is regenerated by using a vacuum pump or other device (42), preparing the packed column for the next step;

A system of electro-valves (8, 9, 33, 34) and check valves (19, 20, 21 and 22) allows to conveniently direct the gas stream.

The recycled xenon (with a concentration above 97%) is stored in a stainless steel reservoir (41). This is achieved either by compressing the gas, or by using a column containing a specific adsorbent (e.g. zeolite 5A). This last solution, allows storing a large amount of xenon in a small volume even at low pressures. A column containing two kilograms of zeolite 5A allowed storing 50 litres (STP) of xenon at 1 bara, while the storing the same quantity in an empty column would require a pressure of 25 bara.

The recycled xenon is reused through the pressurised (8 bar) gas line that feeds the pure xenon (usually in a gas cylinders or in a proper gas line) to the Anaesthesia Gas Machine (AGM). This is performed through a 3-way electro-valve (10) which can be either activated or not; if activated the valve connects the container storing recycled xenon to the Anaesthesia Gas Machine (AGM), if not it connects gas cylinder containing xenon to the Anaesthesia Gas Machine (AGM). By default, the valve is not activated, when so, the Xenon External Recycling Unit (XERU) does not interfere with the Anaesthesia Gas Machine (AGM) supply from the xenon gas cylinder, this constitutes the safer position.

If the Xenon External Recycling Unit (XERU) power supply is cut, if no recycled xenon is available in the External Recycling Unit (XERU), if any abnormal situation occurs or if the anaesthetist decides to, the 3-way valve is deactivated and the anaesthetic gas mixture is fed by the xenon gas cylinder. Under standard operation conditions, the valve is activated if the recycled xenon stored inside the External Recycling Unit (XERU) has a minimum pressure (45) and a minimum purity (5).

If an empty reservoir is used to store the recycled xenon, this can be fed to the Anaesthesia Gas Machine (AGM) using a pressure regulator to set pressure at 8 bar. If an adsorbent filled reservoir is used instead, the stored gas must be previously pressurised at 8 bar (e.g. using a compressor) before fed to the Anaesthesia Gas Machine (AGM) through the 3-way electro-valve.

DESCRIPTION OF THE DRAWINGS

FIG. 1 shows:
1—Vent relief valve of the valve of the Anaesthesia Gas Machine (AGM)
2—Flowmeter
3 to 5—Composition sensor
6 to 12—3-way electro-valve
13—Condensation removal system
14—Gas sterilisation system
15 to 28—Check valve
29 to 31—Compressor
32 to 35—Electro-valve
36, 37—Pressure regulator
38 to 40—Packed column
41—Packed column with heater
42—Vacuum pump
43, 44—Needle valve
45—Pressure sensor
46—Membrane system
47—Input gas line connecting to the xenon gas cylinder
48—Output gas line connecting to the Anaesthesia Gas Machine (AGM)

FIG. 2 shows the adsorbed amount of xenon, oxygen and nitrogen in zeolite 5A as a function of the pure gas pressure. The experience was performed using the volumetric method at 20° C.±1° C., with a mass of adsorbent of 28.9 g; the holding tank volume was 202.8±0.6 cm$^3$, the sample tank volume was 45.4±0.2 cm$^3$ and the adsorbent volume was 12.3±0.2 cm$^3$.

FIG. 3 shows the xenon, oxygen and nitrogen composition of a gas stream leaving a 100 cm$^3$ packed column filled with zeolite 5A, as function of time. The packed column initially evacuated was pressurised and fed with a gas stream containing 70%-24%-6% of xenon-oxygen-nitrogen at a decreasing pressure (from 1.9 bara to 1.4 bara) and a decreasing flowrate (from 120 to 60 cm$^3$/min.)

FIG. 4 shows the xenon, oxygen and nitrogen composition of a gas stream leaving a 1725 cm$^3$ packed column filled with CMS, as function of time. The packed column initially evacuated was pressurised and fed with a gas stream containing 70%-24%-6% of xenon-oxygen-nitrogen at a constant pressure (1.4 bara) and a decreasing flowrate (from 120 to 60 cm$^3$/min.)

BIBLIOGRAPHY

Figure 1:
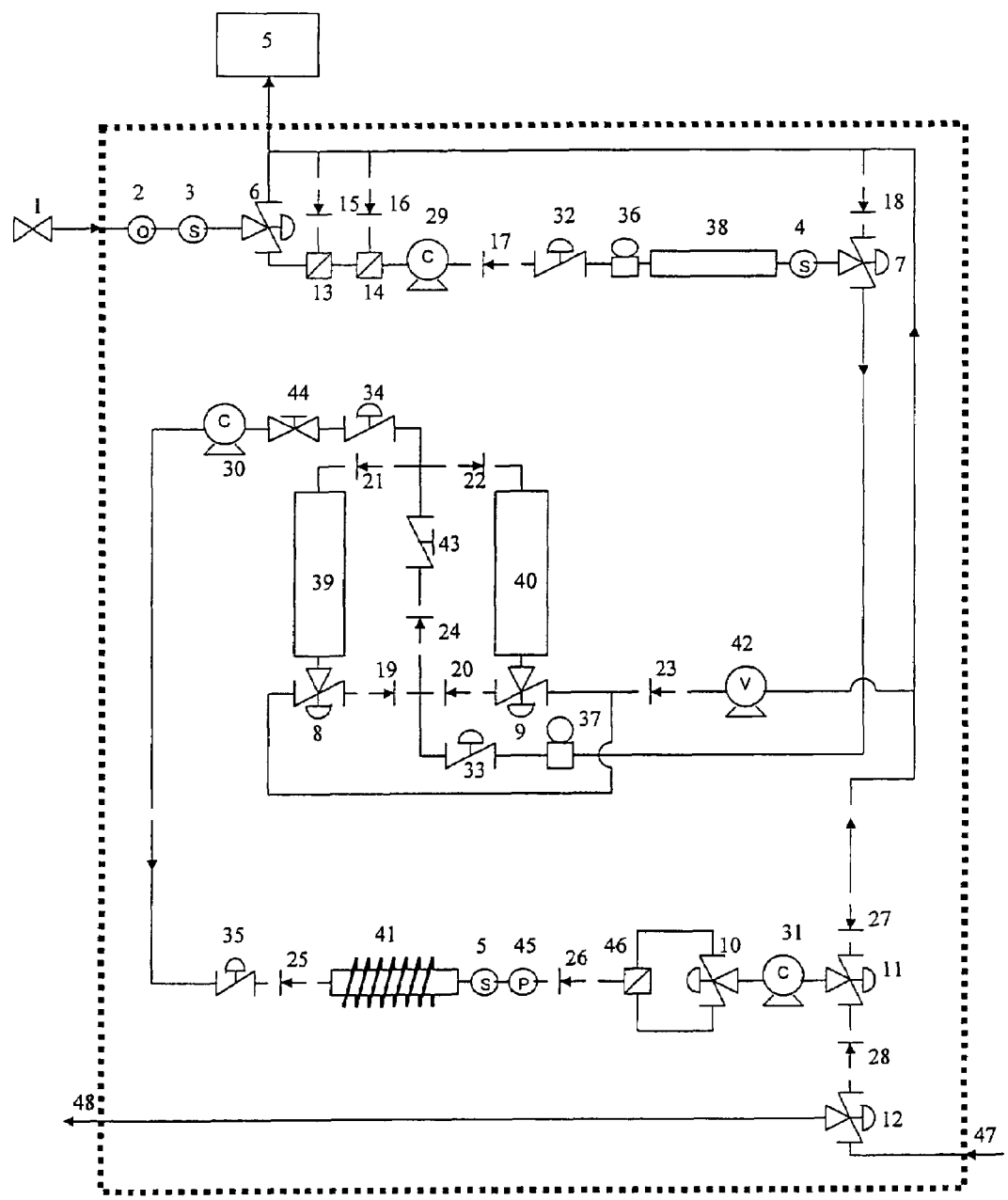
In FIG. 1, a schematic diagram, is proposed as a non confining example of the presented invention.
Figure 2:
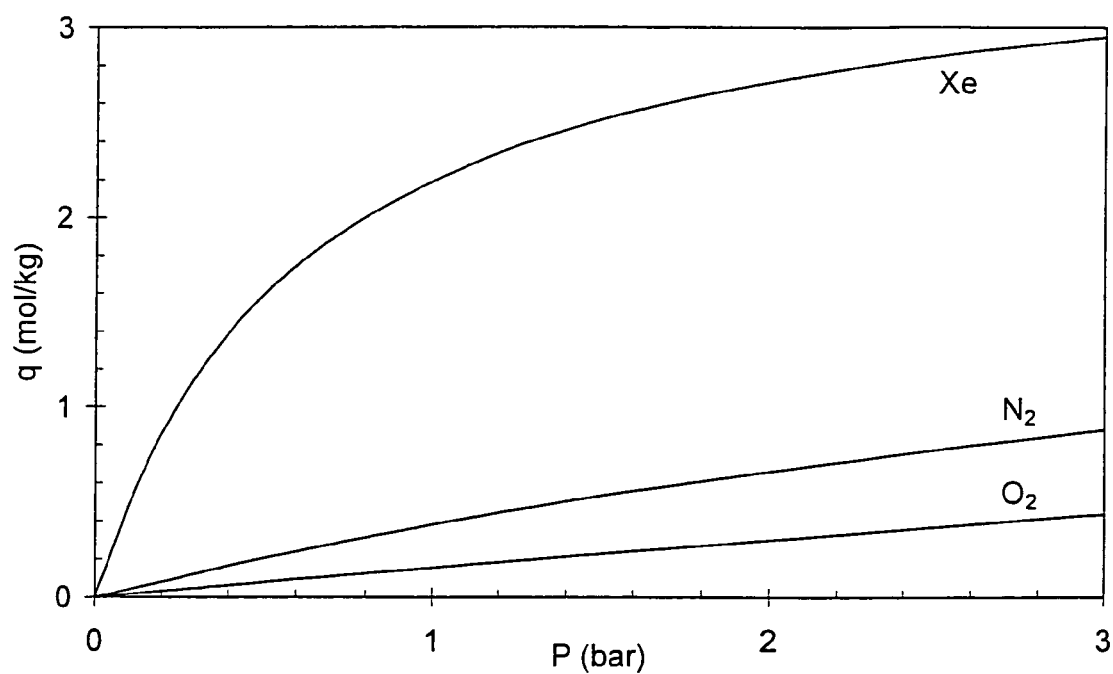
FIGS. 2, 3 and 4, show.
Figure 3:
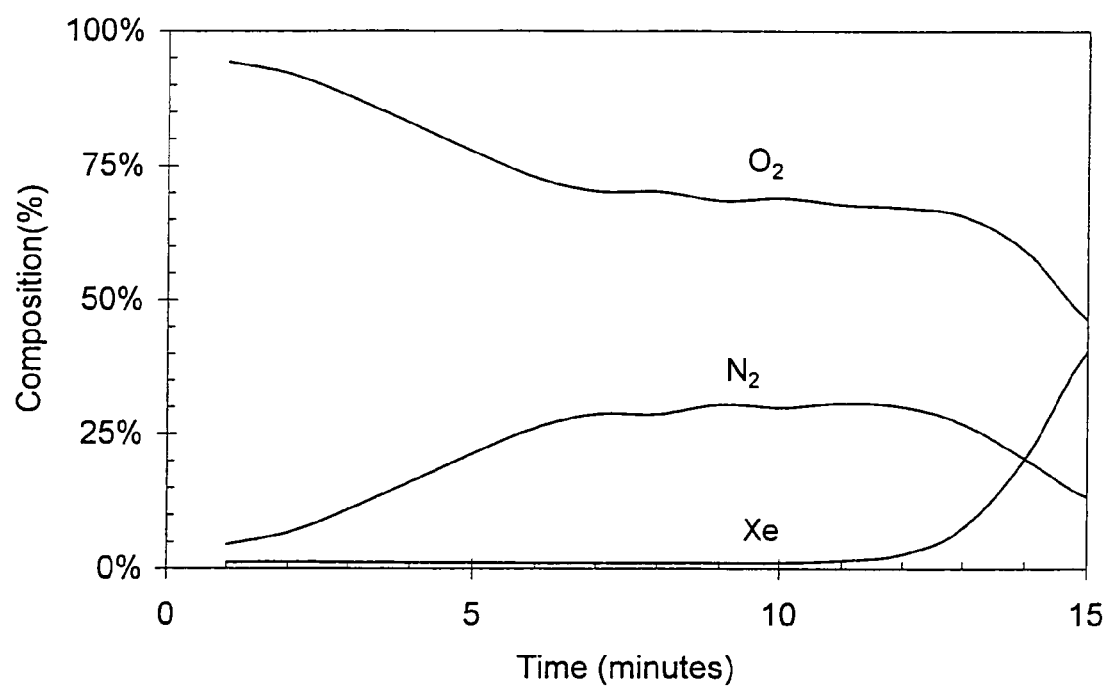
Figure 4:
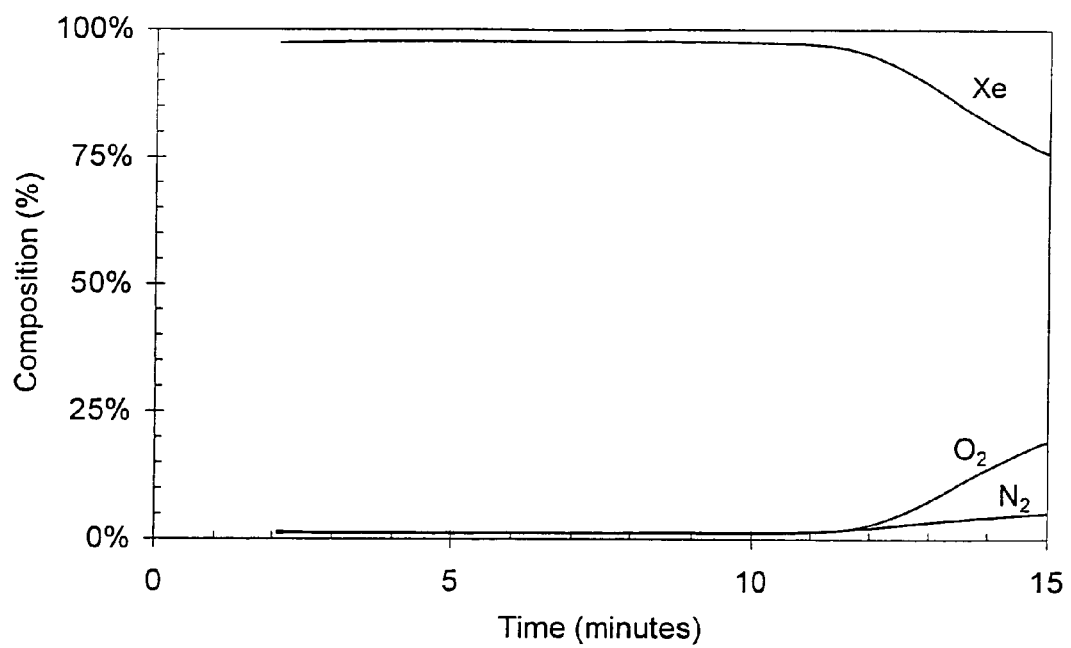

[1]—MENDES, ADÉLIO; "DISPOSITIVO E PROCESSO DE REMOÇÃO DO DIÓXIDO DE CARBONO E DO AZOTO DE UM CIRCUITO ANESTÉSICO FECHADO USANDO XÉNON"; PT102416, 2001.

[2]—HAYAKAWA, SABURO; TAKEUCHI; NAOKO; NAKAMURA, AKIHIRO; "METHOD AND DEVICE FOR ANESTHESIA USING XENON"; JP2001252358, 2001.

[3]—GEORGIEFF, MICHAEL; MARX, THOMAS; BADER, STEFAN; "ANESTHESIA ARRANGEMENT FOR RECOVERING GASEOUS ANESTHETIC AGENTS"; DE5520169; 1996.

[4]—BUROV, N. E.; MAKEEV, G. N.; "METHOD AND DEVICE FOR RECLAIMING XENON FROM NARCOTIC GAS MIXTURE IN ANESTHESIA APPARATUS"; RU204948, 1995

[5]—ESCHWEY, MANFRED; HAMM, REINER; NEU, PETER; SCHMIDT, RENATE; SCHROEDER, GEORG; "ON-LINE RECOVERY OF XENON FROM ANAESTHETIC GAS"; WO9808583, 1998.

[6]—BOSO, LUCA; "PROCESS AND APPARATUS FOR PURIFYING AND RECOVERING XENON AND OTHER NOBLE GASES USED IN ANAESTHETIC SYSTEMS"; WO 9818718, 1998.

[7]—HAMM, REINER; "SEPARATION OF XENON FROM GAS MIXTURES OR REMOVAL OF HIGH PURITY XENON FROM ANAESTHETIC GAS—USING PROCESS HAVING TWO OR MORE SEPARATION STAGES"; EP901985, 1999

[8]—BUROV, N. E.; POTAPOV, V. N.; EFIMOV, V. V.; MAKEEV, G. N.; SURNIN, A. G.; VOVK, S. M.; "METHOD AND DEVICE FOR REGENERATING XENON FROM NARCOTIC GAS MIXTURE USED IN ANESTHESIA APPARATUS"; RU2149033; 2000.

[9]—DRAEGER AEROSPACE GMBH; "SELECTIVE ADSORPTION APPARATUS FOR REMOVING XENON FROM MIXTURE WITH NITROGEN AND OXYGEN, USEFUL IN ANAESTHETIC—USES COMMERCIALLY-AVAILABLE TYPE X, ZSM-5 OR A ZEOLITE OF SPECIFIED GROUP AND PORE SIZE IN COMPACT UNIT WITH FEW COMPONENTS"; DE29817824, 1998.

The invention claimed is:

1. A Xenon External Recycling Unit (XERU), for recycling xenon from a gas mixture released by an Anaesthesia Gas Machine (AGM) using xenon as anaesthetic gas, comprising:
  a) a Selective Recovery System (SRS) that is connected to a vent relief valve of the AGM through a gas line that is able to collect the released gas mixture, provided that it has a minimum flow, a minimum xenon composition, and a pressure variation below a threshold value; wherein the SRS comprises: a shifting system for directing the gas mixture either to a storage or conditioning system, if said gas mixture contains a minimum threshold of xenon concentration, or otherwise to an output line; and a safety system that can override the normal operation of said Selective Recovery System (SRS) purging the gas mixture to the outside;
  b) a condensation removal system;
  c) a gas sterilization system;
  d) an adsorption-based System of Purification (SP), wherein said SP comprises at least one stage able to separate the xenon in said gas mixture with a selective adsorbent;
  e) a composition detector for analyzing the recycled xenon; and
  f) a Recycled Xenon Introduction System (RXIS) that feeds the Anaesthesia Gas Machine (AGM), provided that the recycled xenon has a minimum xenon composition.

2. The XERU, according to claim 1, wherein the output line is selected from the group consisting of:
   a) a line connecting the gas to the outside;
   b) a line connecting the gas to an outside ventilation system;
   c) a line connecting the gas to a scavenger system; and
   d) a line connecting the gas to a recycling unit.

3. The XERU, according to claim 1, wherein said safety system is triggered by any one or more of the group consisting of:
   a) the maximum capacity of treatment/storage of the gas mixture is reached;
   b) the Xenon External Recycling Unit (XERU) is not active;
   c) the pressure variation in the gas line connecting the Anaesthesia Gas Machine (AGM) to the Selective Recovery System (SRS) is above a certain threshold; and
   d) a manual command is given.

4. The XERU, according to claim 1, wherein said System of Purification (SP) comprises:
   a) a packed column containing an adsorbent that selectively adsorbs xenon over oxygen and nitrogen;
   b) a mechanism for driving the gas mixture through the packed column;
   c) a system for detecting composition variations in the gas stream; and
   d) a heating device, associated with the packed column, to facilitate the removal of adsorbed xenon.

5. The XERU of claim 4, wherein the selective adsorbent included in the packed column is zeolite 5A or Li-X.

6. The XERU of claim 4, wherein the non-adsorbed gas stream, with a low xenon concentration, is directed to the atmosphere or to a device that disposes of the non-adsorbed stream.

7. The XERU, according to claim 1, wherein said System of Purification comprises a pair of packed columns, in an arrangement known as "Vacuum Pressure Swing Absorption", wherein:
   a) the packed columns contain an adsorbent for performing the kinetic separation of the xenon from oxygen and nitrogen, by not adsorbing xenon;
   b) the packed columns operate in a 180° out of phase cycle;
   c) each cycle includes the stages: pressurization, production, equalization, and evacuation; and
   d) control is achieved using an automatic system, such as a logical control unit and electro-valves.

8. The XERU, according to claim 7, the use of which comprises the following four steps in a cyclic sequence:
   a) a pressurization step, lasting for 1 to 20 seconds, in which the pressure inside the packed column is increased from a sub-atmospheric pressure to a given pressure, first by using a gas stream from the other column and then using the gas stream to be recycled, keeping closed the column end opposite to the feed end;
   b) a production step, lasting less than 10 minutes, in which the gas stream is fed to one end of the packed column and a rich xenon concentration stream is produced on the other end of the column by retaining the non-xenon components in the adsorbent, finishing this step when the adsorbent has no more capacity to retain the non-xenon fed components;
   c) an equalization step, in which the gas mixture, containing xenon, present in the packed column inter-particular phase is recovered in the second column, by connecting the two columns and allowing the pressurized gas mixture to flow to the evacuated second column until pressure in both columns is partially or totally equalized; and
   d) an evacuation step, succeeding the equalization step, in which the packed column is regenerated by using a vacuum pump or other device, preparing the packed column for the next step.

9. The XERU according to claim 7, wherein the adsorbent included in the packed columns is a Carbon Molecular Sieve.

10. The XERU according to claim 7, wherein the gas stream produced during the evacuation stage, is directed to at least one of the group consisting of:
    a) a line connecting the gas stream to the outside;
    b) a line connecting the gas stream to an outside ventilation system;
    c) a line connecting the gas stream to a scavenger system; and
    d) a line connecting the gas stream to a recycling unit.

11. The Xenon External Recycling Unit (XERU) of claim 1, wherein said System of Purification comprises an arrangement of two or more purification stages.

12. The XERU according to claim 1, wherein the RXIS comprises:
    a) means of connecting the Recycled Xenon Introduction System (RXIS) to a xenon input channel of the Anaesthesia Gas Machine (AGM);
    b) a selection system for directing to the Anaesthesia Gas Machine (AGM) either the recycled xenon, if its purity is above a minimum threshold, or xenon supplied from an external source, otherwise, and
    c) a safety system which can override the normal operation of said Recycled Xenon Introduction System (RXIS), thereby interrupting the feeding of recycled xenon, allowing only the pure xenon from an external source to be fed to the Anaesthesia Gas Machine (AGM).

13. The XERU according to claim 12, wherein said xenon input channel is an anaesthetic gas feed valve.

14. The XERU according to claim 12, wherein said external source is a gas cylinder with pure xenon or a gas mixture containing xenon.

15. The XERU, according to claim 12, wherein the RXIS comprises a safety system, triggered by any one or more of the conditions selected from the group consisting of:
    a) the available amount of recycled xenon, or gas mixture containing xenon, is below a certain threshold;
    b) said Xenon External Recycling Unit (XERU) is not active;
    c) the pressure variation in the gas line connecting said Anaesthesia Gas Machine (AGM) to said Recycled Xenon Introduction System (RXIS) is above a certain threshold; and
    d) a manual command is given.

* * * * *